United States Patent
Togashi

(10) Patent No.: US 11,045,413 B2
(45) Date of Patent: Jun. 29, 2021

(54) OILY SOLID COSMETIC

(71) Applicant: TOKIWA CORPORATION, Nakatsugawa (JP)

(72) Inventor: Shunsuke Togashi, Kawaguchi (JP)

(*) Notice: Subject to any disclaimer, the term of this patent is extended or adjusted under 35 U.S.C. 154(b) by 257 days.

(21) Appl. No.: 16/009,228

(22) Filed: Jun. 15, 2018

(65) Prior Publication Data
US 2018/0369126 A1 Dec. 27, 2018

(30) Foreign Application Priority Data

Jun. 27, 2017 (JP) .............................. JP2017-125411

(51) Int. Cl.
| A61Q 1/06 | (2006.01) |
| A61Q 1/08 | (2006.01) |
| A61K 8/894 | (2006.01) |
| A61K 8/37 | (2006.01) |
| A61K 8/92 | (2006.01) |
| A61Q 1/10 | (2006.01) |
| A61K 8/02 | (2006.01) |
| A61Q 19/00 | (2006.01) |
| A61Q 1/02 | (2006.01) |

(52) U.S. Cl.
CPC ............ A61K 8/894 (2013.01); A61K 8/0216 (2013.01); A61K 8/37 (2013.01); A61K 8/922 (2013.01); A61Q 1/02 (2013.01); A61Q 1/06 (2013.01); A61Q 1/08 (2013.01); A61Q 1/10 (2013.01); A61Q 19/00 (2013.01); A61K 2800/10 (2013.01); A61K 2800/544 (2013.01)

(58) Field of Classification Search
None
See application file for complete search history.

(56) References Cited

U.S. PATENT DOCUMENTS

| 2007/0134181 A1* | 6/2007 | Shimizu | ................. | A61K 8/375 |
| | | | | 424/64 |
| 2007/0134182 A1 | 6/2007 | Shimizu et al. | | |
| 2008/0152678 A1* | 6/2008 | Shah | ....................... | A61K 8/88 |
| | | | | 424/401 |
| 2012/0251605 A1 | 10/2012 | Iimura et al. | | |
| 2015/0216787 A1* | 8/2015 | Hori | ...................... | A61Q 1/04 |
| | | | | 424/59 |
| 2015/0239924 A1 | 8/2015 | Furukawa et al. | | |

FOREIGN PATENT DOCUMENTS

| JP | H8-092036 | 4/1996 |
| JP | H11-502873 | 3/1999 |
| JP | 3890547 | 3/2007 |
| JP | 2007-269760 | 10/2007 |
| JP | 2011-140481 | 7/2011 |
| JP | 2011-148784 | 8/2011 |
| JP | 2012-082188 | 4/2012 |
| JP | 2012-250927 | 12/2012 |
| JP | 2014-070220 | 4/2014 |
| JP | 2017-504644 | 2/2017 |
| WO | 97/025960 | 7/1999 |
| WO | 2011/049248 | 4/2011 |
| WO | 2011/078408 | 6/2011 |
| WO | 2013/100177 | 7/2013 |
| WO | 2015/092632 | 6/2015 |
| WO | 2015/113307 | 8/2015 |
| WO | 2016/046399 | 3/2016 |
| WO | 2017/167667 | 10/2017 |

OTHER PUBLICATIONS

Formulation possibilities with Dow Corning ES-53000 formulation Aid (Year: 2011).*

* cited by examiner

Primary Examiner — Jyothsna A Venkat
(74) Attorney, Agent, or Firm — Soei Patent & Law Firm

(57) ABSTRACT

An oily solid cosmetic contains an alkyl-polyether-modified silicone having a siloxane dendron structure and a dimer acid ester. The oily solid cosmetic may also contain a candelilla wax resin and a low viscosity oil having a viscosity of 5 to 100 mPa·s at 25° C. Example uses of the oily solid cosmetic include makeup cosmetics such as a lipstick, foundation, rouge, concealer, eye shadow, eyeliner, eyebrow, mascara, makeup base, and hair colorant. Additional uses include skin care cosmetics such as lip cream, lip balm, eye cream, moisturizing cream, and sunscreen.

2 Claims, No Drawings

OILY SOLID COSMETIC

CROSS-REFERENCE TO RELATED APPLICATIONS

This application claims the benefit of priority from Japanese Patent Application No. 2017-125411, filed on Jun. 27, 2017, the entire contents of which are incorporated herein by reference.

TECHNICAL FIELD

The present invention relates to an oily solid cosmetic.

BACKGROUND

An oily solid cosmetic containing a solid oil such as wax, a powder, and a liquid oil as constituent ingredients is manufactured to include basic properties such as moldability while filling a cosmetic container during production, smooth application on the skin, persistence of makeup, or the like. Additional properties of the cosmetics depend on the application of the oily solid cosmetic, and in a case of a lip cosmetic such as a lipstick, the lipstick applied to the lips is manufactured so as not to be easily transferred to a surface which comes into contact with the lips, such as a part of a cup.

In response to such demands, cosmetics having so-called transfer resistance, capable of preventing transfer of cosmetics from the skin, have been developed. Previously, there have been proposed a method of blending a volatile ingredient such as a volatile silicone into a cosmetic (see, for example, Japanese Unexamined Patent Publication No. 8-92036 and Japanese Unexamined Patent Publication No. 11-502873), a method of blending a highly viscous oil such as a hydrogenated polyisobutene and a specific organic silicone oil into a cosmetic (see, for example, Japanese Unexamined Patent Publication No. 2011-140481, Japanese Unexamined Patent Publication No. 2012-82188, and Japanese Unexamined Patent Publication No. 2012-250927), and a method of combining a specific dimer acid ester with a specific transfer inhibitor (see, for example, Japanese Unexamined Patent Publication No. 2007-269760).

SUMMARY

However, it has been found that when the cosmetics obtained according to the methods disclosed in the above-mentioned Japanese Unexamined Patent Publication No. 8-92036 and Japanese Unexamined Patent Publication No. 11-502873 are used, lips become easily dried and the cosmetics tend to have inferior usability.

The techniques disclosed in the above-mentioned, Japanese Unexamined Patent Publication No. 2011-140481, Japanese Unexamined Patent Publication No. 2012-82188, and Japanese Unexamined Patent Publication No. 2012-250927, achieve a transfer inhibiting effect by separating the hydrogenated polyisobutene and the organic silicone oil under shear at the time of application. However, due to the easy separation of the cosmetics at a room temperature, filling the cosmetics into a cosmetic container during production is difficult, and further, since the cosmetics are likely to be applied unevenly at the time of application, it is difficult to obtain uniformly applied cosmetic films and to achieve sufficient persistence of makeup.

The technique disclosed in the above Japanese Unexamined Patent Publication No. 2007-269760, causes not only the transfer inhibitor alone to absorb water, but also the specific dimer acid oligomer ester to hold water so as to increase the viscosity of the cosmetic films, whereby transfer of the cosmetics from the skin is inhibited. However, even with the cosmetics disclosed in Japanese Unexamined Patent Publication No. 2007-269760, it cannot be said that the cosmetic exhibits sufficient transfer resistance. Further, it has been noted that the method for merely increasing a viscosity of an oily ingredient impairs the filling ability of the cosmetic into the container.

An object of one or more embodiments of the present invention is to provide an oily solid cosmetic having excellent transfer resistance, filling ability, usability and persistence of makeup.

In order to achieve the object, the oily solid cosmetic may comprise (A) an alkyl-polyether-modified silicone having a siloxane dendron structure and (B) a dimer acid ester.

An oily solid cosmetic in which a polyether-modified silicone having a specific structure and a dimer acid ester are blended may achieve excellent filling ability (moldability), usability and persistence of makeup, in addition to excellent transfer resistance.

From the viewpoint of further improving persistence of makeup, the oily solid cosmetic may further comprise (C) a candelilla wax resin.

Furthermore, from the viewpoint of further improving transfer resistance, the oily solid cosmetic may further comprise (D) a low viscosity oil having a viscosity of 5 to 100 mPa·s at 25° C.

Accordingly, an oily solid cosmetic excellent in transfer resistance, filling ability, usability and persistence of makeup can be provided.

DETAILED DESCRIPTION

An oily solid cosmetic may comprise (A) an alkyl-polyether-modified silicone having a siloxane dendron structure (hereinafter, also referred to as Ingredient (A)), and (B) a dimer acid ester (hereinafter, also referred to as Ingredient (B)).

It is possible to form a cosmetic film excellent in persistence of makeup, and transfer resistance by containing the Ingredient (A) and the Ingredient (B) in the oily solid cosmetic. Furthermore, even without blending ingredients prompting separation or an increase in the viscosity of the cosmetic and volatile ingredients, the oily cosmetic can sufficiently exhibit the above-described effect, and thus obtain satisfactory filling ability and satisfactory usability, by which easy drying of lips is prevented, the cosmetic is smoothly applied, and application unevenness is reduced.

<(A) Alkyl-polyether-modified Silicone having Siloxane Dendron Structure>

Examples of the Ingredient (A) that may be used include a modified silicone in which a silicone dendron group, an alkyl group, and a polyether group are bonded to the silicone chain. As the Ingredient (A), commercially available products such as "ES-5300" (manufactured by Dow Corning Toray Co., Ltd., product name) can be used.

The blending amount of the Ingredient (A) in the oily solid cosmetic may be 0.1 to 20% by mass, and in some embodiments 5 to 20% by mass, based on the total amount of the cosmetic. When the blending amount of the ingredient (A) is within the above range(s), all of the persistence of makeup, the transfer resistance, and the satisfactory usability, by which easy drying of lips is prevented, the cosmetic is smoothly applied, and an even or uniform application of the cosmetic, can be successfully achieved at a high level. In some example embodiments, one or more properties of the cosmetic may be improved by including an amount or content of Ingredient (A) at the smaller example range disclosed above, namely 5 to 20% by mass.

<(B) Dimer Acid Ester>

Examples of the Ingredient (B) include esters of dimer acid obtained by polymerization of two molecules of unsaturated fatty acids. Examples of the unsaturated fatty acid include linoleic acid, linolenic acid, and oleic acid. Also, examples of the ester moiety of such a dimer acid include ones that may be derived from higher alcohols such as cetyl alcohol, oleyl alcohol, stearyl alcohol, isostearyl alcohol, behenyl alcohol, lauryl alcohol, and linoleyl alcohol; dimer diols obtained by polymerizing two molecules of unsaturated alcohols such as dimer dilinoleyl alcohol; compounds derivable from phytosterol; and castor oil. Specific examples thereof include bisstearyl dimer dilinoleyl dimer dilinoleate, bis(behenyl/isostearyl/phytosteryl) dimer dilinoleyl dimer dilinoleate, hydrogenated castor oil dimer dilinoleate, and (phytosteryl/isostearyl/cetyl/stearyl/behenyl) dimer dilinoleate.

Among the above, from the viewpoint of preventing easy drying of lips, a dimer acid ester containing phytosterol is preferable, and bis (behenyl/isostearyl/phytosteryl) dimer dilinoleyl dimer dilinoleate, and (phytosteryl/isostearyl/cetyl/stearyl/behenyl) dimer dilinoleate are more preferable.

From the viewpoint of improving the persistence of makeup and the transfer resistance, the Ingredient (B) preferably contains dimer dilinoleyl ester dimer dilinoleate, it is more preferable to contain bis(behenyl/isostearyl/phytosteryl) dimer dilinoleyl dimer dilinoleate, or bisstearyl dimer dilinoleyl dimer dilinoleate, and it is further more preferable to contain bis(behenyl/isostearyl/phytosteryl) dimer dilinoleyl dimer dilinoleate.

Compounds usable as the Ingredient (B) may be used singly, or two or more thereof may be used in combination.

The compound used for Ingredient (B) may comprise commercially available products used in cosmetics, such as "Plandool-G" (manufactured by Nippon Fine Chemical Co., Ltd., product name) for bis(behenyl/isostearyl/phytosteryl) dimer dilinoleyl dimer dilinoleate, "Plandool-H" (manufactured by Nippon Seika Co., Ltd., product name) for (phytosteryl/isostearyl/cetyl/stearyl/behenyl) dimer dilinoleate, "LUSPLAN DA-DD-IS" (manufactured by Nippon Seika Co., Ltd., product name) for bisstearyl dimer dilinoleyl dimer dilinoleate, and "RISOCAST DA-L" (manufactured by Kokyu Alcohol Kogyo Co., Ltd., product name) for hydrogenated castor oil dimer dilinoleate may be used, respectively.

The blending amount of the Ingredient (B) in the oily solid cosmetic may be 10 to 50% by mass, and in some embodiments 10 to 30% by mass, based on the total amount of the cosmetic. When the blending amount of the ingredient (B) is within the above range(s), all of the persistence of makeup, the transfer resistance, and the usability, by which easy drying of lips is prevented, the cosmetic is smoothly applied, and uniformity of the cosmetic, can be successfully achieved at a high level. In some example embodiments, one or more properties of the cosmetic may be improved by including an amount or content of Ingredient (B) at the smaller example range disclosed above, namely 10 to 30% by mass.

From the viewpoint of further improving persistence of makeup, the oily solid cosmetic may comprise (C) a candelilla wax resin (hereinafter also referred to as Ingredient (C)).

<(C) Candelilla Wax Resin>

Examples of the Ingredient (C) include a candelilla wax fraction containing 65% or more of a resin content obtained by fractional extraction of candelilla wax from an organic solvent such as ethanol (see Japanese Patent No. 3890547). Fractional extraction may be carried out, for example, by heating and dissolving the candelilla wax in ethanol, filtering the crystals that have been precipitated after cooling, and concentrating the filtrate.

The candelilla wax resin may include commercially available products used in cosmetics such as "Candelilla resin E-1" and "Candelilla resin E-2" (both manufactured by Nippon Natural Products Co., product names).

The blending amount of the Ingredient (C) in the oily solid cosmetic may be 0.1 to 5% by mass, based on the total amount of the cosmetic. In other example embodiments, the amount of Ingredient (C) may be 0.1 to 3% by mass, based on the total amount of the cosmetic. In still other embodiments, the amount of Ingredient (C) may be 0.5 to 2% by mass, based on the total amount of the cosmetic. When the blending amount of the Ingredient (C) is within the above range(s), persistence of makeup can further be improved, and satisfactory usability, by which the cosmetic is smoothly applied, and uniformity of application of the cosmetic, can easily be achieved. In some example embodiments, one or more properties of the cosmetic may be improved by including an amount or content of Ingredient (C) at one of the increasingly smaller example ranges disclosed above, such as 0.5 to 2% by mass.

From the viewpoint of further improving secondary transfer resistance, the oily solid cosmetic may comprise (D) a low viscosity oil having a viscosity of 5 to 100 mPa·s at 25° C. (hereinafter, also referred to as Ingredient (D)).

In the present specification, the viscosity is measured with a B type viscometer.

<(D) Low Viscosity Oil having Viscosity of 5 to 100 mPa·s at 25° C.>

Examples of the ingredient (D) include ester oils such as cetyl ethylhexanoate, ethylhexyl palmitate, triethylhexanoin, isotridecyl isononanoate, isostearyl isostearate, neopentyl glycol diethylhexanoate, tri(caprylic capric acid) glyceryl, neopentyl glycol dicaprate, propanediol diisostearate, trimethylolpropane triethylhexanoate, octyldodecyl myristate, and octyldodecyl stearoyl stearate; silicone oils such as dimethicone, and methylphenyl polysiloxane; hydrocarbon oils such as liquid paraffin, squalane, and olefin oligomers; vegetable oils such as sunflower seed oil, jojoba seed oil, and olive oil; higher fatty acids such as isostearic acid; and higher alcohols such as isostearyl alcohol, octyldodecanol, and oleyl alcohol.

The blending amount of the Ingredient (D) in the oily solid cosmetic may be 15 to 80% by mass, based on the total amount of the cosmetic. In other example embodiments, the amount of Ingredient (D) may be 20 to 80% by mass, based on the total amount of the cosmetic. In still other embodiments, the amount of Ingredient (D) may be 20 to 70% by mass, based on the total amount of the cosmetic. When the blending amount of the Ingredient (D) is within the above range(s), it is possible to further improve the transfer resistance and to easily achieve the satisfactory filling ability and satisfactory usability, by which easy drying of lips is prevented and the cosmetic is smoothly applied. In some example embodiments, one or more properties of the cosmetic may be improved by including an amount or content of Ingredient (D) at one of the increasingly smaller example ranges disclosed above, such as 20 to 70% by mass.

From the viewpoint of further improving the usability, with which easy drying of lips is prevented, the content of the volatile ingredient may be 10% by mass or less, and in some examples 5% by mass or less, based on the total amount of the cosmetic. In some example embodiments, one or more properties of the cosmetic may be improved by including an amount or content of the volatile ingredient at the smaller example range disclosed above, namely 5% by mass or less, or by providing an oily solid cosmetic which contains no volatile ingredients.

In the present specification, the term "volatile ingredient" means an oil agent having a boiling point of 250° C. or less at 1 atm (101.325 kPa).

The oily solid cosmetic may further comprises oily ingredients other than the above-mentioned ingredients, and a powder ingredient depending on the application.

<Other Oily Ingredients>

Examples of the other oily ingredients may include solid oils, pasty oils, and high viscosity liquid oils having a viscosity exceeding 100 mPa·s at 25° C. used for cosmetics. These may be used singly, or two or more thereof may be blended in combination to be used. In the present specification, the term "solid oil" means oils that do not flow when inclined at 40° C.

Examples of the solid oil include hydrocarbons such as paraffin wax, microcrystalline wax, and polyethylene; plant-derived fats and oils such as hydrogenated castor oil, hydrogenated jojoba oil, carnauba wax, and rice wax; esters such as glyceryl tribehenate, and cholesterol fatty acid esters; higher fatty acids such as stearic acid, and behenic acid; higher alcohols such as stearyl alcohol, and behenyl alcohol; silicones such as alkyl-modified silicone, and acrylic modified silicone; sugar fatty acid esters such as palmitic acid dextrin, and stearic acid inulin. These may be used singly, or two or more thereof may be blended in combination to be used.

Examples of the pasty oil include vaseline, dipentaerythrityl hexa(hydroxystearate/stearate/rosinate), hydrogenated castor oil isostearate, phytosteryl oleate, sucrose triacetate tetrastearate, dipentaerythrityl tetra(hydroxystearate/isostearate), dipentaerythrityl hexahydroxystearate, glyceryl tri(caprylate/caprate/myristate/stearate), and sucrose hexa(oleate/palmitate/stearate). These may be used singly, or two or more thereof may be blended in combination to be used.

Examples of the high viscosity liquid oil include hydrocarbon oils such as liquid paraffin, squalane, and hydrogenated polyisobutene; ester oils such as diisostearyl malate, polyglyceryl triisostearate, dipentaerythrityl pentaisostearate, and trimethylolpropane triisostearate; vegetable oils such as castor oil; higher alcohols; higher fatty acids; and silicone oils. These may be used singly, or two or more thereof may be blended in combination to be used.

The content of the solid oil in the oily solid cosmetic may be set at 0 to 40% by mass, 0 to 30% by mass, 0.1 to 25% by mass, or 1 to 25% by mass, based on the total amount of the cosmetic.

<Powder Ingredient>

The powder ingredient may comprise an extender powder and coloring pigments.

Examples of the extender powder include an inorganic powder, a synthetic inorganic powder, an organic powder, metal soap, and a synthetic polymer powder. Specific examples thereof include mica, kaolin, sericite, talc, gold mica, synthetic mica, silica, calcium carbonate, magnesium carbonate, aluminum oxide, boron nitride, zinc stearate, aluminum stearate, zinc myristate, polyethylene powder, urethane beads, polymethylmethacrylate, and organopolysiloxane elastomers. In some examples, the extender powder may comprise a spherical powder having an average particle diameter of 1 to 50 µm.

Examples of the coloring pigment include bengara, yellow iron oxide, black iron oxide, cobalt oxide, ultramarine, prussian blue, titanium oxide, zinc oxide, pearl pigments (titanium mica, scale foil, bismuth oxychloride, and the like), organic pigments (red 228, red 226, blue 404, red 202, yellow 4, aluminum lake, and the like), and natural pigment (carmine and safflower).

<Other Ingredients>

Other ingredients used for cosmetic products other than the above described oily ingredient and the powder ingredient may, if necessary, be blended within a range that does not impair the effects of the cosmetic. Additional example ingredients may include moisturizing agents, surfactants, UV absorbers, film forming agents, preservatives, vitamins, beauty ingredients, antioxidants, and perfumes.

The oily solid cosmetic may include makeup cosmetics such as a lipstick, foundation, rouge, concealer, eye shadow, eyeliner, eyebrow, mascara, makeup base, and hair colorant; and skin care cosmetics such as lip cream, lip balm, eye cream, moisturizing cream, and sunscreen.

The oily solid cosmetic may be formed into a stick shape or a pencil shape, or may be directly filled into a container, e.g., an inner tray.

The methods for producing the oily solid cosmetic may include filling a cosmetic bulk obtained by mixing the above-mentioned Ingredients (A) and (B), and in some embodiments, with the Ingredient (C), the Ingredient (D), the oily ingredient, the powder ingredient, and the other ingredient into a predetermined container or mold, and solidifying the cosmetic bulk.

The cosmetic bulk may further comprise a volatile solvent; examples of the volatile solvent include alcohols such as ethanol, propyl alcohol, and isopropyl alcohol; hydrocarbon solvents such as isododecane, and isoparaffin; and silicones such as octamethylcyclopentasiloxane, decamethylcyclopentasiloxane, octamethyltrisiloxane, and decamethyltetrasiloxane. From the viewpoint of preventing easy drying of lips, the content of the volatile ingredient contained in the cosmetic bulk may be 10% by mass or less, based on the total amount of the bulk. In other example embodiments, the content of the volatile ingredient may be 5% by mass or less, based on the total amount of the bulk. In still other embodiments, the content of the volatile ingredient may be 1% by mass or less, based on the total amount of the bulk. The cosmetic bulk can exhibit a sufficient filling ability in such cases, and in some example embodiments, one or more properties of the cosmetic may be improved by including a content of the volatile ingredient at one of the increasingly smaller example ranges disclosed above, such as 1% by mass or less.

Examples of the predetermined container in which the cosmetic bulk is filled include inner trays such as a metal tray and resin tray. These inner trays may be inserted into a compact container after the oily solid cosmetic has been formed. The cosmetic bulk may also be directly filled into a compact container or a jar container. Examples of the method of forming the cosmetic in a stick shape include filling molding methods and extrusion molding methods.

EXAMPLES

Further specific description is provided with reference to the following Examples, but the technical scope is not limited to these Examples.

Prior to the description of the Examples, evaluation methods adopted in each of the Examples will be described.

(1) "Persistence of Makeup", "Usability (Absence of Dryness, Smoothness of Application, Application Unevenness)"

A panel of 20 cosmetics evaluation experts were asked to use cosmetics of the Examples and Comparative Examples, and each of the panels conducted an evaluation at five levels according to the following evaluation criteria with respect to "persistence of makeup" and "usability" (absence of dryness, smoothness of application, application unevenness), giving a score for each of the samples. Thereafter, ratings were determined according to the following criteria using the averages of all scores from the panel.

[Scores: Evaluation Criteria]
5 points: Excellent
4 points: Good
3 points: Fair
2 points: Poor
1 point: Bad

[Evaluation Criteria (Average of Scores)]
A: 4.5 or more
B: 3.5 or more and less than 4.5
C: 1.5 or more to less than 3.5
D: Less than 1.5

(2) "Filling Ability"

The appearances of the cosmetics at the times of filling were visually observed, and the presence or absence of unevenness was determined according to the following evaluation criteria.

[Evaluation Criteria]
A: Unevenness not observed
B: Slight unevenness observed, but nothing disturbing
C: Unevenness observed, slightly disturbing
D: Obvious unevenness observed (3) "(Transfer Resistance)"

Onto a bio-skin plate (manufactured by Beaulax Co., Ltd.), the cosmetics were uniformly applied in areas of 1 cm×3 cm, pieces of paper were pressed against the applied portions, and ratings on transfer of the cosmetics were determined based on visual observation.
A: Almost no transfer to paper
B: Small amount of transfer to paper
C: Apparently noticeable transfer to paper
D: Significant amount of transfer to paper Examples 1 to 10

Ingredients 1 to 9 shown in Table 1 were heated and dissolved at 90 to 100° C. Ingredients 11 to 15 were added thereto, and dispersed with a triple roll. Thereafter, Ingredient 10 was added thereto and dispersed with a disperser. The resulting dispersion was redissolved at 90 to 100° C., degassed, and the obtained product therefrom was filled into a metal tray at 95 to 100° C. and cooled to a room temperature, whereby each of solid lipsticks of Examples 1 to 10 was obtained.

Comparative Examples 1 to 8

Ingredients 1 to 11 shown in Table 2 were heated and dissolved at 90 to 100° C. Ingredients 13 to 17 were added thereto and dispersed with the triple roll. Thereafter, Ingredient 12 was added and dispersed with a disperser. The resulting dispersion was redissolved at 90 to 100° C., degassed, and the product obtained therefrom was filled into the metal tray at 95 to 100° C. and cooled to a room temperature, whereby each of solid lipsticks of Comparative Examples 1 to 8 was obtained.

TABLE 1

| | | Example: 1 | 2 | 3 | 4 | 5 |
|---|---|---|---|---|---|---|
| 1 | Polyethylene A | 8 | 8 | 2.9 | 8 | 8 |
| 2 | Isotridecyl isononanoate | 15 | 26.5 | 80 | 54 | 31 |
| 3 | Dimer acid ester A | 15 | 50 | 10 | 10 | 15 |
| 4 | Dimer acid ester B | — | — | — | — | — |
| 5 | Dimer acid ester C | — | — | — | — | — |
| 6 | Dimer acid ester D | — | — | — | — | — |
| 7 | Pentaerythrityl tetraethylhexanoate | 26 | — | — | — | — |
| 8 | Polyether-modified silicone A | 20 | 5 | 5 | 8 | 10 |
| 9 | Candelilla Resin A | 1 | 0.5 | 0.1 | 5 | 1 |
| 10 | Polymethyl methacrylate (Spherical powder) | 10 | 5 | 1 | 10 | 30 |
| 11 | Red 202 | 0.2 | 0.2 | 1 | 0.2 | 0.2 |
| 12 | Yellow 4 | 0.1 | 0.1 | — | 0.1 | 0.1 |
| 13 | Titanium oxide | 3 | 3 | — | 3 | 3 |
| 14 | Bengara | 1 | 1 | — | 1 | 1 |
| 15 | Iron oxide | 0.7 | 0.7 | — | 0.7 | 0.7 |
| | Total (Parts by mass) | 100 | 100 | 100 | 100 | 100 |
| Evaluation | Persistence of makeup | A | B | B | A | A |
| | Usability (Absence of dryness) | A | A | A | A | A |
| | Usability (Smoothness of application) | A | A | A | B | A |
| | Usability (Application unevenness) | A | A | B | A | A |
| | Filling ability | A | A | A | A | A |
| | Transfer resistance | A | B | B | A | A |

| | | Example: 6 | 7 | 8 | 9 | 10 |
|---|---|---|---|---|---|---|
| 1 | Polyethylene A | 10 | 8 | 8 | 8 | 8 |
| 2 | Isotridecyl isononanoate | 44 | 46 | 46 | 46 | 47 |
| 3 | Dimer acid ester A | — | 20 | — | — | 20 |
| 4 | Dimer acid ester B | 20 | — | — | — | — |
| 5 | Dimer acid ester C | — | — | 20 | — | — |
| 6 | Dimer acid ester D | — | — | — | 20 | — |
| 7 | Pentaerythrityl tetraethylhexanoate | — | — | — | — | — |
| 8 | Polyether-modified silicone A | 10 | 10 | 10 | 10 | 10 |
| 9 | Candelilla Resin A | 1 | 1 | 1 | 1 | — |
| 10 | Polymethyl methacrylate (Spherical powder) | 10 | 10 | 10 | 10 | 10 |
| 11 | Red 202 | 0.2 | 0.2 | 0.2 | 0.2 | 0.2 |
| 12 | Yellow 4 | 0.1 | 0.1 | 0.1 | 0.1 | 0.1 |
| 13 | Titanium oxide | 3 | 3 | 3 | 3 | 3 |
| 14 | Bengara | 1 | 1 | 1 | 1 | 1 |
| 15 | Iron oxide | 0.7 | 0.7 | 0.7 | 0.7 | 0.7 |
| | Total (Parts by mass) | 100 | 100 | 100 | 100 | 100 |
| Evaluation | Persistence of makeup | B | A | A | B | B |
| | Usability (Absence of dryness) | A | A | B | B | A |
| | Usability (Smoothness of application) | A | A | A | A | A |
| | Usability (Application unevenness) | A | A | A | A | A |
| | Filling ability | A | A | A | A | A |
| | Transfer resistance | B | A | A | B | B |

TABLE 2

| | | Comparative Example: 1 | 2 | 3 | 4 |
|---|---|---|---|---|---|
| 1 | Polyethylene A | 8 | 8 | 8 | 8 |
| 2 | Isotridecyl isononanoate | 56 | 66 | 46 | 46 |

TABLE 2-continued

|  |  | 3 | 4 | 5 | 6 |
|---|---|---|---|---|---|
| 3 | Dimer acid ester A | 20 | — | 20 | 20 |
| 4 | Hydrogenated polyisobutene | — | — | — | — |
| 5 | Dipentaerythrityl hexa(hydroxystearate/stearate/rosinate) | — | — | — | — |
| 6 | Polyether-modified silicone A | — | 10 | — | — |
| 7 | Polyether-modified silicone B | — | — | 10 | — |
| 8 | Polyether-modified silicone C | — | — | — | 10 |
| 9 | Polyether-modified silicone D | — | — | — | — |
| 10 | Polyether-modified silicone E | — | — | — | — |
| 11 | Candelilla Resin A | 1 | 1 | 1 | 1 |
| 12 | Polymethyl methacrylate (Spherical powder) | 10 | 10 | 10 | 10 |
| 13 | Red 202 | 0.2 | 0.2 | 0.2 | 0.2 |
| 14 | Yellow 4 | 0.1 | 0.1 | 0.1 | 0.1 |
| 15 | Titanium oxide | 3 | 3 | 3 | 3 |
| 16 | Bengara | 1 | 1 | 1 | 1 |
| 17 | Iron oxide | 0.7 | 0.7 | 0.7 | 0.7 |
|  | Total (Parts by mass) | 100 | 100 | 100 | 100 |
| Evaluation | Persistence of makeup | D | D | D | D |
|  | Usability (Absence of dryness) | B | C | B | B |
|  | Usability (Smoothness of application) | A | A | C | C |
|  | Usability (Application unevenness) | A | A | D | D |
|  | Filling ability | A | C | D | D |
|  | Transfer resistance | D | D | D | D |

|  | Comparative Example: | 5 | 6 | 7 | 8 |
|---|---|---|---|---|---|
| 1 | Polyethylene A | 8 | 8 | 8 | 8 |
| 2 | Isotridecyl isononanoate | 46 | 46 | 46 | 46 |
| 3 | Dimer acid ester A | 20 | 20 | — | — |
| 4 | Hydrogenated polyisobutene | — | — | 20 | — |
| 5 | Dipentaerythrityl hexa(hydroxystearate/stearate/rosinate) | — | — | — | 20 |
| 6 | Polyether-modified silicone A | — | — | 10 | 10 |
| 7 | Polyether-modified silicone B | — | — | — | — |
| 8 | Polyether-modified silicone C | — | — | — | — |
| 9 | Polyether-modified silicone D | 10 | — | — | — |
| 10 | Polyether-modified silicone E | — | 10 | — | — |
| 11 | Candelilla Resin A | 1 | 1 | 1 | 1 |
| 12 | Polymethyl methacrylate (Spherical powder) | 10 | 10 | 10 | 10 |
| 13 | Red 202 | 0.2 | 0.2 | 0.2 | 0.2 |
| 14 | Yellow 4 | 0.1 | 0.1 | 0.1 | 0.1 |
| 15 | Titanium oxide | 3 | 3 | 3 | 3 |
| 16 | Bengara | 1 | 1 | 1 | 1 |
| 17 | Iron oxide | 0.7 | 0.7 | 0.7 | 0.7 |
|  | Total (Parts by mass) | 100 | 100 | 100 | 100 |
| Evaluation | Persistence of makeup | C | D | D | D |
|  | Usability (Absence of dryness) | A | A | C | B |
|  | Usability (Smoothness of application) | A | A | D | C |
|  | Usability (Application unevenness) | A | A | A | A |
|  | Filling ability | B | B | A | A |
|  | Transfer resistance | C | D | D | D |

Details of each of the ingredients in Tables 1 and 2 are as follows:

Polyethylene A: "PERFORMALENE 655" (manufactured by BAKER HUGHES INC., product name, polyethylene)
Isotridecyl isononanoate: a low viscosity oil having a viscosity of 11 mPa·s at 25° C.
Dimer acid ester A: "Plandool-G" (manufactured by Nippon Seika Co., Ltd., product name, bis(behenyl/isostearyl/phytosteryl) dimer dilinoleyl dimer dilinoleate)
Dimer acid ester B: "Plandool-H" (manufactured by Nippon Seika Co., Ltd., product name, (phytosteryl/isostearyl/cetyl/stearyl/behenyl) dimer dilinoleate)
Dimer acid ester C: "LUSPLAN DA-DD-IS" (manufactured by Nippon Seika Co., Ltd., trade name, bisisostearyl dimer dilinoleyldimer dilinoleate)
Dimer acid ester D: "RISOCAST DA-L" (manufactured by Kokyu Alcohol Kogyo Co., Ltd., trade name, hydrogenated castor oil dimer dilinoleate)
Pentaerythrityl tetraethylhexanoate: High viscosity oil having a viscosity of 124 mPa·s at 25° C.
Hydrogenated polyisobutene: High viscosity oil having a viscosity of 85000 mPa·s at 25° C.
Dipentaerythrityl hexa(hydroxystearate/stearate/rosinate): pasty oil
Polyether-modified silicone A: "DOW CORNING (R) ES-5300 FORMULATION AID" (manufactured by Dow Corning Toray Co., Ltd., product name, lauryl PEG-10 tris(trimethylsiloxy)silylethyl dimethicone)
Polyether-modified silicone B: "KF-6028" (manufactured by Shin-Etsu Chemical Co., Ltd., product name, PEG-9 polydimethylsiloxyethyl dimethicone)
Polyether-modified silicone C: "KF-6015" (manufactured by Shin-Etsu Chemical Co., Ltd., product name, PEG-3 dimethicone)
Polyether-modified silicone D: "KF-6038" (manufactured by Shin-Etsu Chemical Co., Ltd., product name, lauryl PEG-9 polydimethylsiloxyethyl dimethicone)
Polyether-modified silicone E: "KF-6048" (trade name, manufactured by Shin-Etsu Chemical Co., Ltd., cetyl PEG/PPG-10/1 dimethicone)
Candelilla Resin A: "Candelilla resin E-2" (manufactured by Nippon Natural Products Co., Ltd., product name, candelilla wax extract) Polymethyl methacrylate (spherical powder): average particle size 6 μm.

As shown in Table 1, in the cosmetic products obtained in Examples 1 to 10, all of the persistence of makeup, the usability (absence of dryness, smoothness of application, application unevenness), the filling ability, and the transfer resistance were rated as "B" or "A".

Example 11

Lipstick

| (Ingredients) | (Blending ratio (mass %)) |
|---|---|
| 1. Polyethylene *1 | 8.0 |
| 2. Candelilla Wax | 2.0 |
| 3. Cetyl ethylhexanoate *2 | 15.5 |
| 4. Triethyl hexanoin *3 | 12.0 |
| 5. Olefin oligomer *4 | 12.0 |
| 6. Dimer acid ester A | 15.0 |
| 7. Polyether-modified silicone A | 10.0 |
| 8. Candelilla Resin A | 1.0 |
| 9. Silica (spherical powder) *5 | 10.0 |
| 10. Mica titanium | 5.0 |
| 11. Bengara coated mica titanium | 5.0 |
| 12. Red 202 | 1.0 |
| 13. Yellow 4 | 0.5 |
| 14. Titanium oxide | 2.0 |
| 15. Bengara | 1.0 |

Details of the above ingredients are as follows.
1: "PERFORMALENE 500" (manufactured by BAKER HUGHES INC., trade name)
2: Viscosity 14 mPa·s at 25° C.
3: Viscosity 30 mPa·s at 25° C.
4: Viscosity 99 mPa·s at 25° C.
5: Average particle diameter 7 μm Ingredients 6 to 8 are the same as those shown in Tables 1 and 2.

<Production Method>

Ingredients 1 to 8 were heated and dissolved at 90 to 100° C. Ingredients 12 to 15 were added thereto, and dispersed with the triple roll. Thereafter, Ingredients 9 to 11 were added thereto and dispersed with the disperser. The resulting dispersion was redissolved at 90 to 100° C., degassed, and the product obtained therefrom was filled into a mold at 95 to 100° C. and cooled to a room temperature and molded. The molded cosmetic was filled into a lipstick container and a lipstick was obtained, whereby a solid lipstick of Example 11 was obtained.

<Evaluation>

Regarding the obtained lipstick, evaluations similar to those of the above Examples were conducted, and it was found that all of the persistence of makeup, the usability (absence of dryness, smoothness of application, and application unevenness), filling ability, and transfer resistance of the lipstick of Example 11 are rated as A.

Example 12

Stick Concealer

| (Ingredients) | (Blending ratio (mass %)) |
|---|---|
| 1. Polyethylene *1 | 2.0 |
| 2. Ceresin | 6.0 |
| 3. Stearoyl inulin | 2.0 |
| 4. Diethylhexanoic acid neopentyl glycol * 2 | 10.0 |
| 5. Ethylhexyl palmitate *3 | 13.5 |
| 6. Isostearyl isostearate *4 | 8.0 |
| 7. Dimer acid ester A | 10.0 |
| 8. Dimer acid ester E *5 | 10.0 |
| 9. Polyether-modified silicone A | 8.0 |
| 10. Candelilla resin A | 0.5 |
| 11. (Vinyl dimethicone/methicone silsesquioxane) Crosspolymer (spherical powder) * 6 | 5.0 |
| 12. (HDI/PPG/polycaprolactone) Crosspolymer (spherical powder) * 7 | 5.0 |
| 13. Disodium stearoyl glutamate treated iron oxide | 0.36 |
| 14. Disodium stearoyl glutamate treated yellow iron oxide | 2.2 |
| 15. Disodium stearoyl glutamate treated titanium oxide | 17.4 |
| 16. Disodium stearoyl glutamate treated black iron oxide | 0.04 |

Details of the above ingredients are as follows.
1: "PERFORMALENE 400" (manufactured by BAKER HUGHES INC., trade name)
2: Viscosity 14 mPa·s at 25° C.
3: Viscosity 13 mPa·s at 25° C.
4: Viscosity 38 mPa·s at 25° C.
5: "LUSPLAN DD-DA 5" (manufactured by Nippon Seika Co., Ltd., trade name dimer dilinoleyl dimer dilinoleate)
6: Average particle size 30 μm
7: Average particle size 15 μm
Ingredient 7, 9, and 10 are the same as those shown in Tables 1 and 2.

<Production Method>

Ingredients 1 to 10 were heated and dissolved at 90 to 100° C. Ingredients 13 to 16 were added thereto and dispersed with the triple roll. Thereafter, Ingredients 11 to 12 were added thereto and dispersed with a disperser. The resulting dispersion was redissolved at 90 to 100° C., degassed, and the product obtained therefrom was filled into a stick shaped container at 95 to 100° C. and cooled to a room temperature, whereby a stick concealer of Example 12 was obtained.

<Evaluation>

Regarding the obtained stick concealer, evaluations similar to those of the above Examples were conducted, and it was found that all of the persistence of makeup, the usability (absence of dryness, smoothness of application, and application unevenness), filling ability, and transfer resistance of the stick concealer of Example 12 are rated as A.

Example 13

Cheek Color

| (Ingredients) | (Blending ratio (mass %)) |
|---|---|
| 1. Synthetic wax *1 | 8.0 |
| 2. Microcrystalline wax | 2.0 |
| 3. Neopentyl glycol diethylhexanoate *2 | 15.0 |
| 4. Glycerol tri(caprylate/caprate) *3 | 14.0 |
| 5. Dimethicone *4 | 15.0 |
| 6. Dimer acid ester A | 15.0 |
| 7. Polyether-modified silicone A | 8.0 |
| 8. Candelala resin A | 1.5 |
| 9. (Diphenyl dimethicone/vinyl diphenyl dimethicone/silsesquioxane) Crosspolymer (Spherical powder) *5 | 15.0 |
| 10. Red 202 | 0.2 |
| 11. Yellow 4 | 1.3 |
| 12. Titanium oxide | 5.0 |

Details of the above ingredients are as follows.
1: "LIP WAX A-4" (manufactured by Nippon Natural Products Co., Ltd., trade name)
2: Viscosity 14 mPa·s at 25° C.
3: Viscosity 23 mPa·s at 25° C.
4: Viscosity 6 mPa·s at 25° C.
5: Average particle size 5 μm
Ingredients 6 to 8 are the same as those shown in Tables 1 and 2.

<Production Method>

Ingredients 1 to 8 were heated and dissolved at 90 to 100° C. Ingredients 10 to 12 were added thereto and dispersed with the triple roll. Thereafter, Ingredient 9 was added and dispersed with a disperser. The resulting dispersion was redissolved at 90 to 100° C., degassed, and the product obtained therefrom was filled into a metal tray at 95 to 100° C. and cooled to a room temperature, whereby a cheek color of Example 13 was obtained.

<Evaluation>

Regarding the obtained cheek color, evaluation similar to those of the Examples were conducted, and it was found that all of the persistence of makeup, the usability (absence of dryness, smoothness of application, and application unevenness), filling ability, and transfer resistance of the cheek color of Example 13 were rated as A.

It is to be understood that not all aspects, advantages and features described herein may necessarily be achieved by, or included in, any one particular example embodiment. Indeed, having described and illustrated various examples herein, it should be apparent that other examples may be modified in arrangement and detail. We claim all modifications and variations coming within the spirit and scope of the subject matter claimed herein.

What is claimed is:

1. An oily solid cosmetic comprising:
   (A) lauryl PEG-10 tris(trimethylsiloxy)silylethyl dimethicone;
   (B) bis(behenyl/isostearyl/phytosteryl) dimer dilinoleyl dimer dilinoleate;
   (C) a candelilla wax resin; and
   (D) ester oil selected from the group consisting of cetyl ethylhexanoate, ethylhexyl palmitate, triethylhexanoin, isotridecyl isononanoate, isostearyl isostearate, neopentyl glycol diethylhexanoate, tri(caprylic/capric acid) glyceryl, neopentyl glycol dicaprate, propanediol diisostearate, trimethylolpropane triethylhexanoate, octyldodecyl myristate, and octyldodecyl stearoyl stearate, having a viscosity of 5 to 100 mPa·s at 25° C., wherein
   a blending amount of the (A) lauryl PEG-10 tris(trimethylsiloxy)silylethyl dimethicone is 5% to 20% by mass based on a total amount of the oily solid cosmetic,
   a blending amount of the (B) bis(behenyl/isostearyl/phytosteryl) dimer dilinoleyl dimer dilinoleate is 10% to 30% by mass based on the total amount of the oily solid cosmetic,
   a blending amount of the (C) candelilla wax resin is 0.5% to 5% by mass based on the total amount of the oily solid cosmetic,
   a blending amount of the (D) ester oil is 20% to 70% by mass based on the total amount of the oily solid cosmetic, and
   the oily solid cosmetic comprises no volatile solvent having a boiling point of 250° C. or less at 1 atm (101.325 kPa).

2. The oily solid cosmetic according to claim 1, further comprising a powder ingredient.

* * * * *